United States Patent [19]
Yee

[11] 3,955,928
[45] May 11, 1976

[54] PREGNANCY TEST
[76] Inventor: Hugh Yee, 4201 Frostwood, Troy, Mich. 48084
[22] Filed: Aug. 15, 1975
[21] Appl. No.: 604,926

[52] U.S. Cl. ............................................. 23/230 B
[51] Int. Cl.² ................. G01N 21/14; G01N 31/02; G01N 31/08; G01N 33/16
[58] Field of Search ...................... 23/230 B; 424/7

[56] References Cited
UNITED STATES PATENTS
3,615,229   10/1971   Besch et al. ...................... 23/230 B OTHER PUBLICATIONS
Frankel et al., ed., Gradwohl's Clinical Laboratory Methods and Diagnosis, C. V. Mosby Co., 1970; pp. 256, 273 of interest.

R. L. Searcy, Diagnostic Biochemistry, McGraw-Hill, 1969; pp. 205–206 of interest.

Hawk et al., Practical Physiological Chemistry, McGraw-Hill, 1954; pp. 762+ of interest.

Primary Examiner—Robert M. Reese
Attorney, Agent, or Firm—Hauke, Patalidis & Dumont

[57] ABSTRACT

A process for determining pregnancy wherein the concentration of estrogen steroids in the urine is evaluated by spectrophotometric measurement.

15 Claims, No Drawings

PREGNANCY TEST

BACKGROUND OF THE INVENTION

It is generally known that the concentration of estrogen steroids in the female increases appreciably during pregnancy. It is also well established that the stage, as well as the fact of pregnancy, may be determined by measuring the amount of estrogen steroids present in the urine. Besch et al U.S. Pat. No. 3,615,229, issued on Oct. 26, 1971, for "Use of Oxalic Acid for the Hydrolysis of Steriod Conjugates in Pregnancy" discloses a method for the determination of pregnancy estrogen concentration comprising the hydrolysis and cleavage of conjugated steroids found in urine by treating with organic acids. The estrogens thereby liberated may then be measured under standard colorimetric methods by comparison with standard concentrations of estriol. However, this method has the disadvantage of necessitating time consuming steps such as color development and color extraction.

SUMMARY OF THE INVENTION

The present invention pertains to a process for determining pregnancy by measurement of the estrogens present in urine utilizing known spectrophotometric procedures wherein the estrogen steroids are separated from the urine, hydrolyzed, extracted from the urine and formed into chromogens. The present method for determining pregnancy overcomes the disadvantages of the prior art by providing a relatively simple procedure whereby the estrogen steroid content of a urine sample may be analyzed with maximum speed, accuracy and efficiency either manually or automatically.

DESCRIPTION OF THE PREFERRED EMBODIMENT

According to the present invention, estrogen steroids may initially be separated from the urine by one of the following procedures: (a) the estrogen steroids may be separated from the urine by precipitation with ammonium sulfate solution by centrifugation; (b) the estrogen steroids may be separated from the urine by solvent extraction with an ethyl ether-ethanol solution wherein ammonium sulfate is added to the urine sample before the introduction of the solvent; or (c) the separation of the estroid steroids may also be effected by means of a neutral ion-exchange chromatography column. The urine sample is passed through the chromotography column whereby the estrogen steroids are retained in the column. The estrogen steroids may then be eluted from the column with the methanol.

Following the separation of the estrogen steroids from the urine sample, hydrolysis is accomplished utlizing an enyme mixture of beta-glucuronidase and phenol sulfatase in an acetate buffered solution. The hydrolyzed steroids may then be extracted with ethyl ether and the ether evaporated to yield a residue of the estrogen steroids.

The chromogen development may then be accomplished by reacton of the estrogen steroids by a coupling of the phenolic groups of the steroid molecules with either 3-methyl-2-benzothiazolinone hydrazone hydrochloride (MBTH) or 4-aminoantipyrine. This reaction is then followed by oxidation using ceric salts or ferric salts or ammonium persulfate. After the chromogen formation is completed, the solution is buffered with an ethylene diamine tetraacetic acid disodium salt (EDTA) borate solution. Spectrophotometric measurements may then be made at any wavelength from 520 to 550 nm.

According to the present invention, the concentration of estrogen present in the urine sample is determined by comparison of the absorbance values of the urine sample with those of estrogen standards of known concentration.

The practice of the present invention is further illustrated by reference to the following detailed example:

EXAMPLE I

Separation of the steroids from urine

A separation of the estrogen steroids from the sample urine may be effected by any one of the following procedures:

a. According to the first procedure, a urine sample of 5 ml may be acidified with 0.1 ml 6 normal sulfuric acid solution. To this acidified solution is added 3.5 g. ammonium sulfate (70% w/v). The mixture thereby obtained is centrifuged at 17,000 rpm at 0°–5°C for thirty minutes. The supernatant liquid is then discarded and the precipitate dissolved in 5 ml water. The dissolving of the precipitate may be facilitated by the addition of a few drops of 1 normal sodium hydroxide to the water.

b. In a second procedure for the separation of the estrogen steroids from the urine, a urine sample is acidified by adding 0.1 ml 6 normal sulfuric acid per 5 ml urine sample. 2.5 g ammonium sulfate for each 5 ml of urine sample is then added to the acidified solution. The urine sample is then extracted with 10 ml of 3;1 w/v ethyl ether-ethanol solvent (3:1 v/v ether: alcohol). The solvent layer is then separated and evaporated at 55°C until dry. The estrogen steroid residue is then dissolved in 5 ml of water.

c. According to the third procedure for the separation of the estrogen steroids from urine, the urine sample is acidified by adding 0.1 ml 6 normal sulfuric acid per 5 ml urine sample. The acidified urine sample is then passed through a neutral ionexchange resin column of Amberlite XAD-2, 1 cm diameter × 5 cm height. The estrogen steroids collected in the ion-exchange column is then eluted using 6 ml of methanol. The methanol-steroid solution thereby obtained is collected and evaporated at 55°C until dry. The estrogen steroid residue is then dissolved in 5 ml water.

Hydrolysis

The estrogen steroids obtained from the urine sample by means of one of the above described separation procedures are then hydrolyzed. The hydrolysis is effected by the addition of an acetate buffer of pH 4.7 2 mol/liter concentration and Glusulase to the purified urine extract. 1 ml acetate buffer and 0.5 ml of Glusulase are required for each 5 ml of the purified urine extract solution. The mixture thus obtained is then incubated at 55°C for 120 minutes. The hydrolyzed steroids are then extracted with 25 ml ethyl ether which is then washed with a 1 molar solution of potassium carbonate and water. An aliquot of the ether is then evaporated to dryness at 55°C.

Chromogen Formation and Measurement

The chromogen formation and the spectrophotometric measurement may be effected by either manual or automated means.

A. Manual Method

According to the manual method, the purified, hydrolyzed steroid residue obtained from 1 ml urine is first dissolved in 1 ml methanol. The 1 ml aliquot of the methanol solution is transferred to a test tube. A reagent blank consisting of 1 ml methanol and 1 ml samples of each estriol standard of known concentration to be used as comparative standards are then prepared and pipeted into labeled tubes. The chromogen development is accomplished in the sample urine and in all estrogen standards by the addition of 1 ml 0.15% w/v, 3-methyl-2-benzothiazolinone hydrazone hydrochloride (MBTH) to all tubes. After the addition of MBTH, the contents of each tube is mixed and allowed to stand for five minutes. 1 ml 0.2% w/v ceric ammonium sulfate solution is then added to all tubes. Each tube is then mixed and again allowed to stand for five minutes. 2 ml EDTA-borate buffer is added to all tubes and mixed therewith. The absorbance spectrum of the sample urine, obtained at 540 nm, is then compared against the reagent blank and the estriol standards of known concentration.

B. Automated Method

According to the automated method, the purified, hydrolyzed estrogen steroid residue obtained from 2 ml urine is dissolved in ethanol and water in a ratio of 0.5 ml ethanol and 1.5 ml water. The solution is mixed therewith. Reagent lines are then attached to 0.05% w/v 3-methyl-2-benzothiazolinone hydrazone hydrochloride (MBTH), 0.2% w/v ceric ammonium sulfate and 0.3% w/v ethylene diamine tetraacetic acid disodium salt (EDTA). An AutoAnalyzer system currently commercially available from Technicon Corporation of Tarrytown, New York, comprising a sampler, pump, colorimeter and recorder, is used to evaluate the estrogen content of the sample urine. This system uses the technique of continuous flow analysis. The samples, continuously following one another through a system of tubing, are brought together with reagents under controlled conditions, causing a chemical reaction that is quantitatively measurable. In the system, filters of 530 nm are positioned in relation to the aperture. The manifold is then placed on the pump and reagents pumped therethrough. After stability is reached, the zero and 100% transmittance baselines are set. According to this method, sample specimens and standards may be tested at a rate of fifty per hour.

It is important to note that under both the manual and automated methods 4-aminoantipyrine may be used instead of 3-methyl-2-benzothiazolinone hydrazone hydrochloride (MBTH) and ferric salts or ammonium persulfate may be used in place of ceric ammonium sulfate according to the enumerated procedures.

It will thus be seen that I have provided by my invention a novel and improved process for determining pregnancy.

What is claimed is:

1. A process for determining pregnancy by measurement of the estrogens present in urine, comprising the steps of:
   a. separating the estrogen steroids from the urine;
   b. hydrolyzing the separated estrogen steroids;
   c. extracting the estrogen steroids from the urine;
   d. forming the estrogen steroid extract into chromogens; and
   e. evaluating the concentration of the estrogen steroids by spectrophotometric measurements.

2. The process defined in claim 1 wherein the step of separating the estrogen steroids from the urine is accomplished by precipitation with ammonium sulfate and centrifugation.

3. The process of claim 1 wherein the step of separating the estrogen steroids from the urine is accomplished in a neutral ion-exchange resin chromotography column and then eluted from the resin column with methanol.

4. The process of claim 1 wherein the step of hydrolyzing the separated estrogen steroids is performed with an enzyme mixture of beta-glucuronidase and phenol sulfatase.

5. The process of claim 1 wherein the step of hydrolyzing the separated estrogen steroids is performed in an acetate buffered solution.

6. The process of claim 1 wherein the extracting of the estrogen steoids from the urine is effected with ethyl-ether, the ether then being evaporated to yield an estrogen steroid residue.

7. The process as defined in claim 1 wherein the step of evaluating the concentration of the estrogen steroids is performed by spectrophotometric measurement at wavelengths of the order of 520-550 nm and comparison of the absorbance values thereby obtained with those of estrogen standards of known concentrations.

8. The process of claim 1 wherein the step of separating the estrogen steroids from the urine is effected by solvent extraction with a 3:1 ratio ethy ether-ethanol solvent mixture of the urine sample with ammonium sulfate.

9. The process defined in claim 8 wherein after the chromogen forming there is included the further step of buffering with an EDTA-borate solution.

10. The process of claim 1 wherein the step of forming chromogens is accomplished by the reaction of the estrogen steroids by a coupling of the phenolic group of estrogen steroid molecules with a conjugating agent, followed by the further step of oxidation.

11. The process of claim 10 wherein the conjugating agent comprises 3-methyl-2-benzothiazolinone hydrazone hydrochloride.

12. The process of claim 10 wherein the conjugating agent comprises 4-aminoantipyrine.

13. The process defined in claim 10 wherein the further step of oxidation is accomplished with ceric salts.

14. The process defined in claim 10 wherein the further step of oxidation of the estrogen steroids is accomplished by treatent with ferric salts.

15. The process defined in claim 10 wherein the further step of oxidation is accomplished by treatment with ammonium persulfate.

* * * * *